(12) United States Patent
Tsuto et al.

(10) Patent No.: US 6,288,251 B1
(45) Date of Patent: Sep. 11, 2001

US006288251B1

(54) PROCESS FOR PREPARING ALKYL ESTERS OF FATTY ACIDS FROM FATS AND OILS

(75) Inventors: Keiichi Tsuto, Muko; Guo-Tang Liu, Kyoto, both of (JP)

(73) Assignee: Lonford Development Limited, Kyoto-Fu (JP)

( * ) Notice: Subject to any disclaimer, the term of this patent is extended or adjusted under 35 U.S.C. 154(b) by 0 days.

(21) Appl. No.: 09/555,941

(22) PCT Filed: Oct. 1, 1999

(86) PCT No.: PCT/JP99/05431

§ 371 Date: Aug. 14, 2000

§ 102(e) Date: Aug. 14, 2000

(87) PCT Pub. No.: WO00/20541

PCT Pub. Date: Apr. 13, 2000

(30) Foreign Application Priority Data

Oct. 6, 1998 (JP) .................................................. 10-284261

(51) Int. Cl.⁷ ...................................................... C11C 1/00
(52) U.S. Cl. .............................................................. 554/169
(58) Field of Search ............................................... 554/169

(56) References Cited

U.S. PATENT DOCUMENTS 5,972,057    10/1999    Hayafuji et al. ....................... 44/388
6,090,959    7/2000    Hirano et al. ......................... 554/169

FOREIGN PATENT DOCUMENTS

| 61-14044 | 1/1986 | (JP) . |
|---|---|---|
| 6-313188 | 11/1994 | (JP) . |
| 7-197047 | 8/1995 | (JP) . |
| 7-310090 | 11/1995 | (JP) . |

OTHER PUBLICATIONS

Patent Abstract of Japan, Publication No. 07197047 A, Publication date Aug. 1, 1995, 1 page.
Patent Abstract of Japan, Publication No. 07310090 A, Publication date Nov. 28, 1995, 1 page.
Patent Abstracts of Japan, Publication No. 61014044 A, Publication date Jan. 22, 1986, 1 page.
Patent Abstracts of Japan, Publication No. 06313188 A, Publication date Nov. 8, 1994, 1 page.

*Primary Examiner*—Deborah D. Carr
(74) *Attorney, Agent, or Firm*—Rosenthal & Osha, L.L.P.

(57) ABSTRACT

Provided is a process for producing a fatty acid alkylester through a transesterification of triglyceride contained in a fat and oil by causing the fat and oil and an alcohol to react with each other. In this process, the reaction is performed in an atmosphere in which the alcohol is in super-critical state in the absence of a metal alkali catalyst and an acid catalyst. This makes it possible to eliminate a pre-treatment process for esterifying free fatty acids contained in the fat and oil and, in addition, to eliminate or simplify recovering and refining processes of the reaction product by suppressing the by-production of a fatty acid soap.

4 Claims, No Drawings

PROCESS FOR PREPARING ALKYL ESTERS OF FATTY ACIDS FROM FATS AND OILS

This application is a 371 of PCT/JP99/0543 filed Oct. 1, 1999.

TECHNICAL FIELD

The present invention relates to a process for preparing or producing a fatty acid alkylester which can be effectively used as a fuel oil for diesel engines, for instance, through a transesterification of triglyceride contained in a variety of fats and oils including plant oils such as rape oil, sesame oil, soybean oil, corn oil, sunflower oil, palm oil, palm kernel oil, coconut oil, corn oil and safflower oil, animal oils such as beef fat, lard and fish oil, and, in addition, waste edible oils, i.e., spent oils of these plant and animal oils, with an alcohol.

BACKGROUND ART

Currently, large quantities of edible fats and oils as mentioned above are used in our country. Although a certain part of spent oils (aforementioned waste edible oils) is recycled as a raw material for producing soap, for example, they are mostly conveyed to a refuse dump without being recovered to be burned together with other combustible wastes or disposed in landfills together with incombustible wastes in actuality.

It has been known that a fatty acid alkylester could be obtained by subjecting major ingredients of fats and oils such as monoglyceride, diglyceride and triglyceride, to a transesterification with an alkyl alcohol (Handbook of Organic Chemistry, published by Gihodo Shuppan, 1988, pp. 1407–1409). Various attempts using the transesterification have thus far been made to produce an alkylester usable as a diesel engine fuel oil from the aforementioned oils and fats, as disclosed in Japanese Unexamined Patent Publication Nos. 7-197047 and 7-310090, for example. It has not been possible, however, to obtain any alkylester complying with current requirements of the Japanese Industrial Standards (JIS) imposed on light oil products by such prior art technology.

In a typical industrial process for a production of a fatty acid ester from triglyceride, in particular triglyceride contained in natural fats and oils, a fatty acid glyceride is caused to react with a lower alcohol in the presence of a metal alkali catalyst at normal pressure and at a temperature near the boiling point of the lower alcohol. The reaction process, however, uses the metal alkali catalyst dissolved in the reaction solution. Therefore, the metal alkali catalyst remains dissolved in the liquid reaction product obtained by this reaction process, resulting in a problem that it is difficult to separate and recover the metal alkali catalyst from the liquid reaction product.

There are another problems as follows. Natural fats and oils generally contain a large amount of free, i.e., unesterified, fatty acids. The amount of free fatty acids depends on origins of the raw material fats and oils and processes of them. On the average, it is more than 3 weight % of the fats and oils. When a metal alkali catalyst is used in the reaction solution having a large amount of free fatty acids, a fatty acid soap may be generated as a by-product of the transesterification, resulting in the need of an excessively large amount of the metal alkali catalyst. Alternatively, the fatty acid soap makes it difficult to separate a fatty acid ester layer from a glycerin layer in the liquid reaction product. To solve these problems, a pre-treatment process for removing the free fatty acids from the reaction solution is necessary for a transesterification of a fatty acid glyceride with an alcohol in the presence of the metal alkali catalyst.

To solve the above-mentioned problems, Japanese Unexamined Patent Publication No. 61-14044 discloses a process of transforming the free fatty acids into a fatty acid ester in the presence of an acid catalyst as the pre-treatment process for removing the free fatty acids. That is, in this process, the free fatty acids are pre-treated to be transformed into an ester, followed by a transesterification of a fatty acid glyceride in the presence of a metal alkali catalyst. However, when the transesterification is performed with the acid catalyst, which has been used in the pre-treatment process, remaining in the reaction solution, a part of the metal alkali catalyst to be used for the transesterification is neutralized by such a remained acid catalyst. Thus, there exists a problem that such a transesterification requires an increased amount of the metal alkali catalyst to compensate for the neutralized part of the metal alkali catalyst.

In addition, Japanese Unexamined Patent Publication No. 6-313188, for example, suggests a process for producing a fatty acid ester in which a solid acid catalyst is used to eliminate the need of the above-mentioned pre-treatment process. However, acid catalysts including the solid acid catalyst have a serious drawback, that is, their catalytic activity is lower than that of metal alkali catalysts in the transesterification of fats and oils. Thus, there exists a problem that the transesterification using acid catalysts needs a larger catalyst amount.

The present invention is aimed at overcoming the aforementioned problems residing in the prior art technology. It is therefore an object of the invention to provide a process for preparing or producing a fatty acid alkylester from fats and oils, in which it is possible to eliminate the pre-treatment process for esterifying the free fatty acids contained in the fats and oils and, by suppressing the by-production of a fatty acid soap, to eliminate or simplify recovering and refining processes of the reaction product.

DISCLOSURE OF THE INVENTION

According to a main feature of the present invention, in a process for producing a fatty acid alkylester through a transesterification of triglyceride contained in a fat and oil by causing the fat and oil and an alcohol to react with each other, the reaction between the fat and oil and the alcohol is performed in an atmosphere in which the alcohol is in super-critical state in the absence of metal alkali and acid catalysts.

In a preferred form of the invention, the transesterification is performed in a tube reactor through which the fat and oil and the alcohol are passed continuously to react with each other. In such a case that the tube reactor is used, the liquid hourly space velocity of triglyceride in the tube reactor is preferably set to 2 to 240/hr. In addition, the preferable alcohol may be a lower alcohol having 1 to 5 carbon atoms per molecule, from the viewpoint that the process for the present invention is particularly useful for the production of high quality fatty acid lower alkylester to be used as a diesel engine fuel oil.

BEST MODE FOR CARRYING OUT THE INVENTION

The inventors have performed an intensive study from a various point of view to find out a solution of the foregoing problems of the prior art. As a result, it has been found that an alkylester can be effectively produced from triglyceride contained in a fat and oil in the absence of a metal alkali catalyst and an acid catalyst by reacting the fat and oil with an alcohol in an atmosphere in which the alcohol is in a super-critical state. According to the process for the present invention, since none of a metal alkali catalyst and an acid catalyst is used for the reaction, eliminated can be the need of a pre-treatment process for esterifying free fatty acids contained in the fat and oil. In addition, using no metal alkali catalyst can eliminate or simplify the recovering and refining processes of the reaction product by suppressing the by-production of a fatty acid soap.

According to the present invention, the fats and oils include natural plant oils and animal oils. As plant oils, coconut oil, palm oil, palm kernel oil, soybean oil, rape oil or the like can be used. As animal oils, beef fat, lard, fish oil or the like can be used. In addition, the fats and oils may include waste edible oils, i.e., spent oils of these natural oils for a particular purpose. Although these fats and oils can be used singly or in combination, it is desirable to use waste edible oils to promote the recycling of resources.

On the other hand, as the alcohol to react with the fats and oils, it is preferred to use an alcohol having 1 to 5 carbon atoms per molecule such as methyl alcohol, ethyl alcohol, propyl alcohol and isopropyl alcohol, from the viewpoint of the production of lower alkylester to be used as a high quality diesel engine fuel oil. Of these, methyl alcohol is most preferable, because it costs low and can be recovered more easily.

What is most characteristic of the present invention is performing the transesterification using the above-mentioned raw materials in an atmosphere in which the alcohol is in a super-critical state. The reasons why the process according to the characteristic has the above-mentioned effects have been considered as follows.

In the case that methyl alcohol is used as the alcohol, if the methyl alcohol is under the condition for making the methyl alcohol be in a super-critical state, the methyl alcohol dissociates into $CH_3O^-$ and $H^+$ ions so that it is activated. And then the proton ($H^+$) also activates triglyceride. Consequently, it is considered that the transesterification between methyl alcohol and triglyceride proceeds effectively. The inventors have tested the effects through experiments and found that, when methyl alcohol is used, the methyl alcohol can be in a super-critical state in the presence of fats and oils under a condition of 250° C. or more and 9 MPa or more, thereby allowing the transesterification to proceed without a catalyst under such a condition.

Another technology has also been known in which the reaction efficiency of the transesterification can be improved by performing the transesterification at high temperature and high pressure. "JAOCS" (vol. 61, no. 2, p343, 1984), for instance, discloses a transesterification using methyl alcohol under a condition of 240° C., 9 MPa. However, the transesterification in this prior art technology is supposed to be performed in the presence of a metal alkali catalyst. In addition, under the above-mentioned prior art condition, the coexistence of the fats and oils in the reaction solution prevents the methyl alcohol from being in a super-critical state. As to the prior art technology, the inventors have confirmed that the transesterification hardly proceeds without a catalyst under such a condition. In order to make an alcohol, e.g., methyl alcohol in the above-mentioned example, be in a super-critical state, the relationship between temperature and pressure is also important. Considering this, the condition of the above-mentioned prior art technology may not satisfy such an appropriate relationship between temperature and pressure for making methyl alcohol be in a super-critical state. Therefore, the alcohol cannot be chemically-activated sufficiently under the prior art condition and, thereby, this prior art technology needs a metal alkali catalyst for the transesterification.

The pressure and temperature in the process for the present invention are not specifically limited, if they meet the condition for making the alcohol completely be in a super-critical state. The condition depends on the kind of the alcohol that is used. In the case that a lower alkyl alcohol is used, the condition is generally made as the following pressure and temperature ranges: the reaction temperature is usually within a range of 250 to 300° C., preferably 250 to 280° C.; the pressure is generally within a range of 3 to 15 MPa, preferably 5 to 13 MPa. When the temperature and pressure are lower than these ranges, the alcohol cannot be satisfactory kept in a super-critical state. On the other hand, when the temperature is higher than the range, a large amount of the reaction product maybe thermally decomposed. Further, when pressure is greater than the range, such high pressure results in a drawback of being uneconomical. As explained above, it is obviously important to further satisfy the appropriate relationship between the temperature and pressure in order to keep the alcohol in super-critical state, even if respective values are fall in the above mentioned ranges.

To cause triglyceride and the alcohol to react with each other, although a batch reaction is possible, preferred is a continuous reaction in which a reaction time under the above-mentioned condition of high temperature and high pressure is controlled more easily. In particular, under a condition of higher than 250° C., it is essential to control the reaction time within 30 minutes, preferably 5 minutes, in order to suppress the thermal decomposition of glycerin or the like. Thus, in a preferred form of the present invention, the transesterification is performed in a tube reactor through which the raw materials, i.e., fats and oils and alcohol, are passed continuously to react with each other.

When the tube reactor is used, the liquid hourly space velocity of triglyceride in the reactor is preferably set to 2 to 240/hr. In the case that the liquid hourly space velocity is lower than 2/hr, the productivity per unit volume of the reactor decreases, thereby being uneconomcal. On the other hand, in the case that the liquid hourly space velocity is greater than 240/hr, a satisfactory high reaction rate cannot be obtained. The more preferable liquid hourly space velocity, therefore, is 12 to 120/hr. In the process for the present invention, though the reaction may proceed sufficiently even in a short reaction time due to such a high reaction temperature, the preferable reaction time is at least 0.25 minute or more. This is because the reaction may not reach an equilibrium state within a reaction time of less than 0.25 minute. The above-mentioned liquid hourly space velocity is defined as a supply amount by volume of triglyceride at 15° C., 1 atm.

The suitable molar ratio of the alcohol to triglyceride in this process is 1.2 to 50 times, more preferably 1.2 to 30 times, as much as the amount stoichiometrically required for transesterification of the triglyceride. In the case that the molar ratio is less than 1.2 times as much as the required amount, it is difficult to keep the alcohol in super-critical state throughout the reaction. In the other case that the molar ratio is more than 50 times as much as the required amount, there exist uneconomical problems such as a low efficiency per volume of the reactor and an increased amount of the alcohol to be recovered.

The liquid reaction product obtained by the above-mentioned reaction contains glycerin and a lower alcohol in addition to a fatty acid ester, i.e., a final product of the present process. During the reaction, glycerin in the reaction solution slightly decreases the equilibrium reaction rate, since the solubility of glycerin to the fat and oil increases due to the alcohol in the supercritical state. The desired reaction rate, however, can be attained by a multistage reaction process, in which the reaction temperature or pressure is lowered on the way of the reaction to separate and remove a layer of the glycerin and then raised again to perform the rest of the reaction.

The liquid reaction product flowed out of the continuous reactor is supplied into a distiller to remove the alcohol therein, followed by a general separation process such as a centrifugal separation and a stationary separation to separate an oil layer (a fatty acid ester) and a glycerin layer (glycerin) in the liquid reaction product. When the oil layer contains the raw material oil that remains unreacted, the oil layer may be distilled to obtain a high quality fatty acid ester by removing the unreacted raw material oil.

EXAMPLES

The invention is now described in further detail with reference to some practical examples of its embodiment. It is to be understood that the mode of carrying out the invention is not limited to the following practical examples, but various modifications may be made therein within the spirit and scope of the invention.

Example 1

75 g of the total weight of edible rape oil and edible soybean oil (manufactured by The Nissin Oil Mills, Ltd.) and 72 g of methyl alcohol (9 times by mole as much as the amount stoichiometrically required for reacting with triglyceride contained in these oils) were mixed in a 300 ml autoclave that is made of stainless steel. The mixture was heated to keep it at 260° C. for 10 minutes. In this step, the pressure of the mixture was set to 8.4 MPa. Then, the mixture was quenched to separate a glycerin layer and an oil layer in the mixture. The methyl ester production ratio in the oil layer was 54% by a measurement using a gas chromatography.

Comparative Example

A reaction was carried out in the same manner as in Example 1 except that a reaction temperature was set to 240° C. In this reaction, the pressure was set to 8.1 MPa. Then, the same analysis as Example 1 was made and the obtained fatty acid methyl ester production ratio of the oil layer was 3%.

Example 2

69 g of unrefined palm oil having an acid value of 6 and 97 g of methyl alcohol (10 times by mole as much as the amount stoichiometrically required for reacting with triglyceride contained in the unrefined palm oil) were mixed in the same container as used in Example 1. The mixture was heated to keep it at 280° C. for 10 minutes. In this step, the pressure of the mixture was set to 11 MPa. Then, the same analysis as Example 1 was made and the obtained methyl ester production ratio in the oil layer was 55%.

Example 3

Into a stainless steel pipe having a diameter of 10 mm and a length of 100 mm, continuously fed were 1.5 g per minute of the same fats and oils as used in Example 1 and 0.76 g per minute of methanol (5 times by mole as much as the amount stoichiometrically required for reacting with triglyceride contained in the fats and oils). The liquid hourly space velocity of triglyceride in the pipe was set to 13.5/hr. The reaction temperature was kept at 270° C. and the pressure was controlled to 12 MPa with an outlet control valve of the pipe.

The obtained reaction product was separated into a glycerin layer and an oil layer, followed by the analysis of the oil layer. As a result, the methyl ester production ratio of the oil layer was 60%.

Industrial Applicability

According to the aforementioned process for the present invention, it is possible to perform a transesterification between a fat and oil and an alcohol efficiently without using a catalyst such as a metal alkali catalyst and an acid catalyst, by reacting the fat and oil with the alcohol in an atmosphere in which the alcohol is in a super-critical state. Because of no use of a catalyst, eliminated can be a pre-treatment process for esterifying free fatty acids contained in the fat and oil or removing then from the fat and oil. A refining process for removing a catalyst, which has been needed in the conventional processes, can also be eliminated. Thus, processes of the transesterification can be considerably simplified or eliminated. The process for the present invention is particularly useful for the production of a lower alkylester to be used as a diesel engine fuel oil.

What is claimed is:

1. A process for producing a fatty acid alkylester through a transesterification of triglyceride contained in a fat and oil by causing the fat and oil and an alcohol to react with each other, wherein the reaction between the fat and oil and the alcohol is performed in an atmosphere in which the alcohol is in a super-critical state in the absence of a metal alkali catalyst and an acid catalyst.

2. The process according to claim 1, wherein the fat and oil and the alcohol are passed continuously through a tube reactor to react with each other.

3. The process according to claim 2, wherein a liquid hourly space velocity of triglyceride in the tube reactor is set to 2 to 240/hr.

4. The process according to any of claims 1 to 3, wherein the alcohol is a lower alcohol having 1 to 5 carbon atoms per molecule.

* * * * *